United States Patent [19]

Chan

[11] Patent Number: 5,172,705
[45] Date of Patent: Dec. 22, 1992

[54] SMOKING COMPOSITIONS CONTAINING AN OXALATE FLAVORANT-RELEASE ADDITIVE

[75] Inventor: Geoffrey W. Chan, Chesterfield, Va.

[73] Assignees: Philip Morris Incorporated, New York, N.Y.; Philip Morris Products Inc., Richmond, Va.

[21] Appl. No.: 765,311

[22] Filed: Sep. 25, 1991

[51] Int. Cl.$^5$ .............................. A61B 15/30
[52] U.S. Cl. ................. 131/276; 131/278
[58] Field of Search ................ 131/276, 278

[56] References Cited

U.S. PATENT DOCUMENTS

| | | | |
|---|---|---|---|
| 3,211,157 | 10/1965 | Rowland | 131/276 |
| 4,753,924 | 6/1988 | Brunke et al. | 131/276 |
| 4,827,012 | 5/1989 | Christenson et al. | 558/260 |
| 4,992,106 | 2/1991 | Christenson et al. | 131/276 |

FOREIGN PATENT DOCUMENTS

| | | | |
|---|---|---|---|
| 0039063 | 4/1981 | Japan | 131/276 |
| 0175484 | 10/1983 | Japan | 131/276 |
| 0002175 | 1/1985 | Japan | 131/276 |

Primary Examiner—Paul Prebilic
Attorney, Agent, or Firm—James E. Schardt

[57] ABSTRACT

In one embodiment this invention provides smoking compositions which contain a novel oxalate ester flavorant-release additive.

Under cigarette smoking conditions, a combustible filler additive such as a methyl 4-oxo-$\beta$-ionyl oxalate

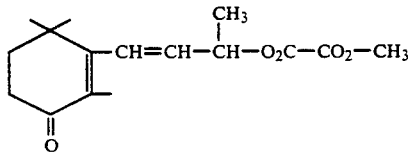

pyrolyzes and releases megastigma-5,7,9-trien-4-one as a natural flavorant component of the cigarette smoke.

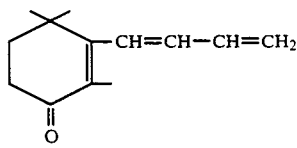

12 Claims, No Drawings

SMOKING COMPOSITIONS CONTAINING AN OXALATE FLAVORANT-RELEASE ADDITIVE

BACKGROUND OF THE INVENTION

Megastigmatrienone [as a 3,5,5-trimethyl-4-(2-butenylidene)cyclohex-2-en-1-one mixture of isomers] is a component of Burley, Turkish and Greek tobacco, as reported in Tobacco Science, 16, 107 (1972); Helv. Chim. Acta, 55, 1866 (1972); Acta Chem. Scand., 26, 2573 (1972); and Tobacco Science, 18, 43–48 (1974), and contributes to the overall flavor characteristics of tobacco.

Megastigmatrienones as a class of natural fragrant tobacco components are described in U.S. Pat. Nos. 4,753,924 and 4,827,012.

Megastigma-4,6,8-trien-3-one(1) can be considered a dehydration product of 3-oxo-o-ionol(2), which also is a constituent of tobacco:

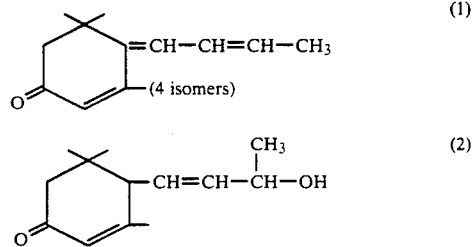

Megastigma-4,6,8-trien-3-one has a tendency to polymerize, and is a difficult chemical compound to store or formulate.

Of background interest with respect to the present invention are technical publications concerned with thermolysis of oxalate esters. Pyrolysis studies of oxalate esters such as benzyl oxalates and diallyl oxalates are reported by W. S. Trahanovsky and coworkers in publications which include J Org. Chem., 32, 2287 (1967); J. Am. Chem. Soc., 90. 2839 (1968); Tetrahedron Lett., 3627 (1968); J. Am. Chem. Soc., 92, 7174 (1970); J. Org. Chem., 36, 3575 (1971); and Chem. Commun., 102 (1971). The thermal decomposition of dialkyl oxalates is described by G. J. Karabatsos et al in J. Org. Chem., 30, 689 (1965) and J. Am. Chem. Soc., 91, 3324 (1969).

It is characteristic of organic compounds employed as tobacco flavorants is the prior art that the respective derivatives have the disadvantage of both high volatility and low odor threshold. Both of these properties significantly restrict the extent that these organoleptic materials can be utilized as flavorants in tobacco compositions.

There is continuing research effort to develop improved smoking compositions which contain a new and efficient low volatility flavorant-release additive, and which generate mainstream smoke with natural flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking compositions having incorporated therein a flavorants release additive which under normal smoking conditions yields pyrolysis constituents which impart improved natural tobacco flavor to mainstream smoke and improved aroma to sidestream smoke.

It is a further object of this invention to provide novel oxalate compounds of low volatility which are adapted to be incorporated into cigarette fillers, and which under normal smoking conditions release a natural tobacco flavorant constituent into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0002–5 weight percent, based on the total weight of filler, of a flavorant-release additive corresponding to the formula:

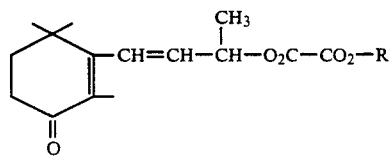

where R is a $C_1$–$C_8$ alkyl substituent.

In another embodiment this invention provides a smoking composition comprising an admixture of (1) combustible filler selected from natural tobacco, reconstituted tobacco and tobacco substitutes, and (2) between about 0.0002–5 weight percent, based on the total weight of filler, of bis-(4-oxo-β-ionyl) oxalate as a flavorant-release additive:

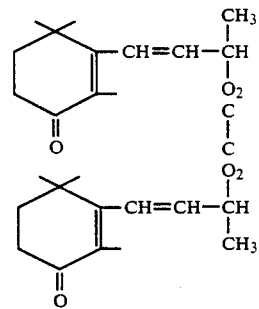

In another embodiment this invention provides a smoking composition comprising an admixture of (1) combustible filler selected from natural tobacco, reconstituted tobacco and tobacco substitutes, and (2) between about 0.0002–5 weight percent, based on the total weight of filler, of a flavorant-release additive corresponding to the formula:

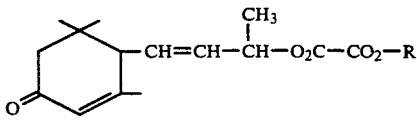

where R is a $C_1$–$C_8$ alkyl substituent.

In another embodiment this invention provides a smoking composition comprising an admixture of (1)

combustible filler selected from natural tobacco, reconstituted tobacco and tobacco substitutes, and (2) between about 0.0002-5 weight percent, based on the total weight of filler, of bis-(3-oxo-α-ionyl) oxalate as a flavorant-release additive:

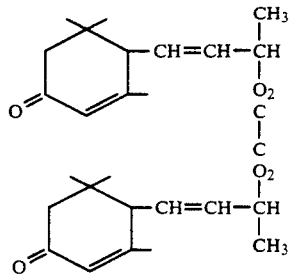

In another embodiment this invention provides a smoking composition comprising an admixture of (1) combustible filler selected from natural tobacco, reconstituted tobacco and tobacco substitutes, and (2) between about 0.0002-5 weight percent, based on the total weight of filler, of a flavorant-release additive responding to the formula:

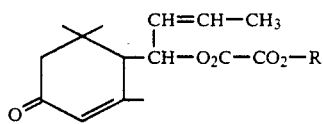

where R is a $C_1$-$C_8$ alkyl substituent.

In another embodiment this invention provides a smoking composition comprising an admixture of (1) combustible filler selected from natural tobacco, reconstituted tobacco and tobacco substitutes, and (2) between about 0.0002-5 weight percent, based on the total weight of filler, of bis-(3-oxo-α-damascyl) oxalate as a flavorant-release additive:

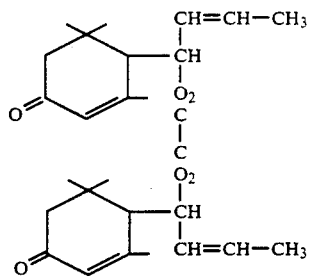

In another embodiment this invention provides a smoking composition comprising an admixture of (1) combustible filler selected from natural tobacco, reconstituted tobacco and tobacco substitutes, and (2) between about 0.0002-5 weight percent, based on the total weight of filler, of a flavorant-release additive corresponding to the formula:

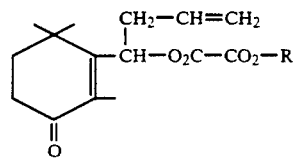

where R is a $C_1$-$C_8$ alkyl substituent.

In another embodiment this invention provides a smoking composition comprising an admixture of (1) combustible filler selected from natural tobacco, reconstituted tobacco and tobacco substitutes, and (2) between about 0.0002-5 weight percent, based on the total weight of filler, of bis-[1-(2,6,6-trimethyl-3-oxo-1-cyclohexenyl-3-buten-1-yl]oxalate as a flavorant-release additive:

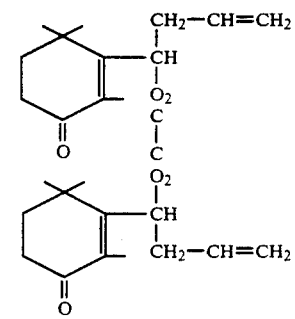

In another embodiment this invention provides an oxalate ester corresponding to the formulae:

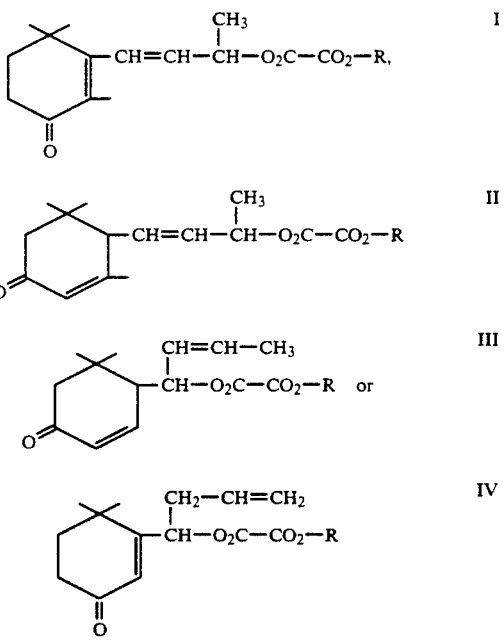

where R is a $C_1$-$C_8$ alkyl substituent such as methyl, ethyl, propyl, isopropyl, butyl, isobutyl, 2-butyl, pentyl, hexyl, 2-hexyl, heptyl, octyl, isooctyl, and the like. In a further embodiment this invention provides the bis-ol oxalates corresponding to formulae I-IV as represented above.

Preparation of Oxalate Ester Compounds

An invention oxalate ester is prepared by reacting a selected carotinoid alcohol derivative with oxalyl halide under caralyzed esterification conditions:

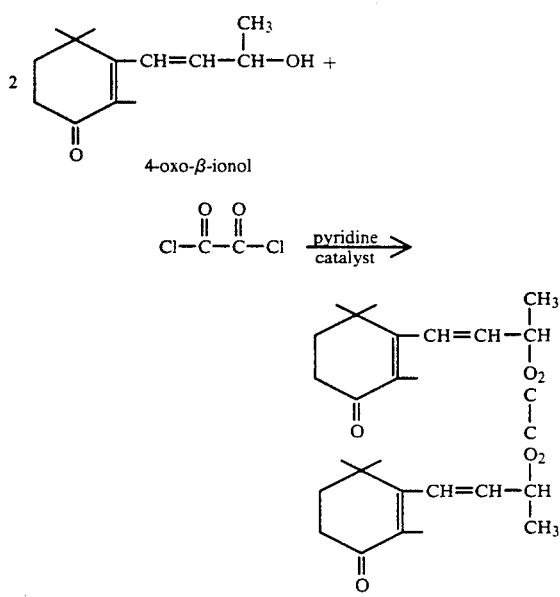

Preparation Of Smoking Compositions

In a further embodiment, this invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a flavorant-release additive corresponding to Formula I, Formula II, Formula III or Formula IV, or a corresponding bis-ol diester derivative as previously defined above.

The invention flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein.

An invention flavorant-release additive also can be incorporated in the paper wrapper of cigarette sidestream smoke under smoking conditions.

An invention oxalate ester compound as described above, when incorporated in a smoking composition, is a low volatility additive which under normal smoking conditions pyrolyzes and releases a volatile megastigmatrienone constituent which enhances the flavor and aroma of low delivery cigarette smoke.

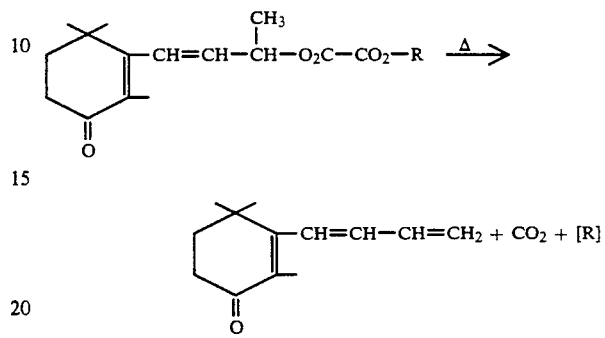

The present invention oxalate esters are stable and odorless compounds at ambient temperature. In addition, the oxalate esters decompose at a relatively low pyrolysis temperature (e.g., 130°–300° C.) to release a megastigmatrienone product in a higher yield than is obtained by pyrolysis of corresponding megastigmatrienone-releasing monoester or carbonate ester derivatives.

The following Examples are further illustrative of the present invention. The specific ingredients are presented as being typical, and various modifications can be derived in view of the foregoing disclosure within the scope of the invention.

EXAMPLE I

Methyl 4-oxo-β-ionyl oxalate

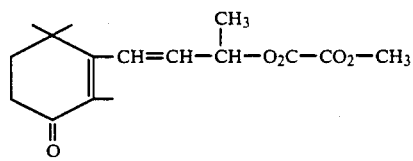

To a chilled solution (0° C.) of 4-oxo-β-ionol (5 g, 24 mmol), pyridine (3.8 g, 48 mmol) and dimethylaminopyridine (0.586 g, 2.4 mmol) in 10 mL of dichloromethane was added dropwise a solution of methyl oxalyl chloride (3.55 g, 29 mmol) dissolved in 5 mL of dichloromethane. After addition was completed, another 10 mL portion of dichloromethane was added. The mixture was stirred for about 18 hours at room temperature. Crushed ice was added to the mixture, and the organic and aqueous phases were separated. The organic phase was washed successively with dilute hydrochloric acid, water, saturated sodium bicarbonate solution, and saturated sodium chloride solution. The product solution was dried over anhydrous magnesium sulfate. The product was isolated by fractional distillation (b.p. 116° C. 0 2 torr) to yield 4.5 g of the title compound. An analytical sample was purified by preparative high performance liquid chromatography, and NMR and IR spectra confirmed the structure.

EXAMPLE

Ethyl 4-oxo-β-ionyl oxalate

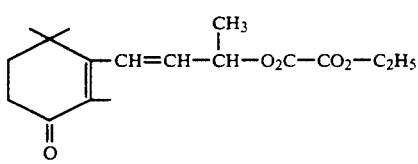

To a chilled (0° C.) solution of 4-oxo-β-ionol (5 g, 24 mmol), pyridine (3.8 g, 48 mmol) and dimethylaminopyridine (0.586 g, 4.8 mmol) in 20 mL of ethyl acetate was added dropwise a solution of ethyl oxalyl chloride (3.96 g, 29 mmol) dissolved in 5 mL of ethyl acetate. The mixture was stirred for about 18 hours at room temperature. Crushed ice was added to the mixture, and the organic portion was separated from the aqueous phase. The organic layer was washed successively with dilute hydrochloric acid, water, and saturated sodium bicarbonate solution, and dried over anhydrous magnesium sulfate. The recovered product was purified by preparative high performance liquid chromatography to yield 5.5 g of the title compound, and NMR and IR spectra confirmed the structure.

EXAMPLE III

Bis-(4-oxo-β-ionyl) oxalate

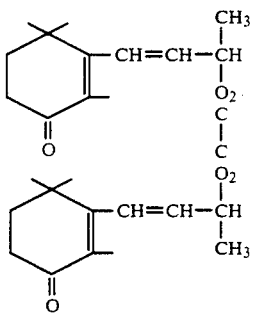

A chilled solution (0° C.) of 4-oxo-β-ionol (10 g, 50 mmol), pyridine (7.6 g, 96 mmol) and dimethylaminopyridine (0.586 g, 4.8 mmol) in 20 mL of ethyl acetate was prepared in a reactor, and a solution of oxalyl chloride (3.08 g, 24 mmol) in 5 mL of ethyl acetate was added dropwise. The mixture was stirred for about 18 hours at room temperature. Crushed ice was added to the mixture, and the organic and aqueous phases were separated. The organic phase was washed successively with dilute hydrochloric acid, water, and saturated sodium bicarbonate solution. The product solution was dried over anhydrous magnesium sulfate.

The product was purified by preparative high performance liquid chromatography to yield 9.5 g of the title compound, and NMR and IR spectra confirmed the structure.

EXAMPLE IV

Methyl 3-oxo-α-ionyl oxalate

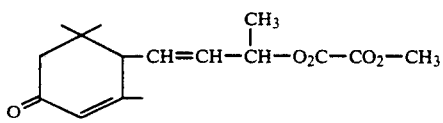

To a chilled (0° C.) solution of 3-oxo-α-ionol (5 g, 24 mmol), pyridine (3.8 g, 48 mmol) and dimethylaminopyridine (0.586 g, 4.8 mmol) in 20 mL of ethyl acetate was added dropwise a solution of methyl oxalyl chloride (3 55 g, 29 mmol) dissolved in 5 mL of ethyl acetate. The mixture was stirred for about 18 hours at room temperature. Crushed ice was added to the mixture, and the organic portion was separated from the aqueous phase. The organic layer was washed successively with dilute hydrochloric acid, water, and saturated sodium bicarbonate solution, and dried over anhydrous magnesium sulfate. The desired product was purified by preparative high performance liquid chromatography, to yield 6.0 g of the title compound, and NMR and IR spectra confirmed the structure.

EXAMPLE V

Ethyl 3-oxo-α-ionyl oxalate

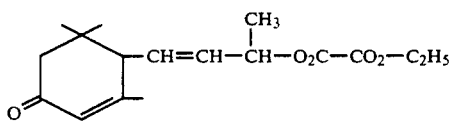

To a chilled (0° C.) solution of 3-oxo-α-ionol (5 g, 24 mmol), pyridine (3.8 g, 48 mmol) and dimethylaminopyridine (0.586 g, 4.8 mmol) in 20 mL of ethyl acetate was added dropwise a solution of ethyl oxalyl chloride (3.96 g, 29 mmol) dissolved in 5 mL of ethyl acetate. Following the procedures of Example IV, the product was recovered and purified by preparative high performance liquid chromatography to yield 6.1 g of the title compound. NMR and IR spectra confirmed the structure.

EXAMPLE VI

Bis-(3-oxo-α-ionyl) oxalate

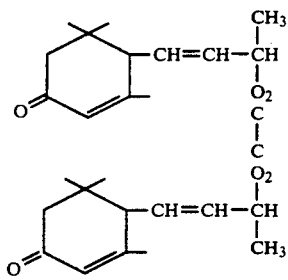

To a chilled (0° C.) solution of 3-oxo-α-ionol (10 g, mmol), pyridine (7.6 g, 96 mmol) and dimethylaminopyridine (0.586 g, 4.8 mmol) in 20 mL of ethyl acetate was added dropwise a solution of oxalyl chloride (3.08 g, 24 mmol) dissolved in 5 mL of ethyl acetate. Following the procedures of Example IV, the product was recovered and purified by preparative high performance liquid chromatography to yield 9.8 g of the title compound. NMR and IR spectra confirmed the structure.

EXAMPLE VII

Methyl 3-oxo-α-damascyl oxalate

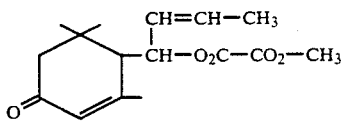

To a chilled (0° C.) solution of 3-oxo-α-damascol (1 g, 4.8 mmol), pyridine (758 mg, 9.6 mmol) and dimethylaminopyridine 0.96 mmol) in 4 mL of ethyl acetate was added dropwise a solution of ethyl oxalyl chloride (710 mg, 5.8 mmol) dissolved in mL of ethyl acetate. The mixture was allowed to stir for minutes at room temperature. Crushed ice and 5 mL of hexane were added to the mixture, and the organic portion was separated from the aqueous phase. The organic layer was washed successively with diluted hydrochloric acid, water, and saturated sodium bicarbonate solution, and dried over anhydrous magnesium sulfate. The product was purified by preparative high performance liquid chromatography to yield 1.0 g of the title compound. NMR and IR spectra confirmed the structure.

EXAMPLE VIII

Bis-(3-oxo-α-damascyl) oxalate

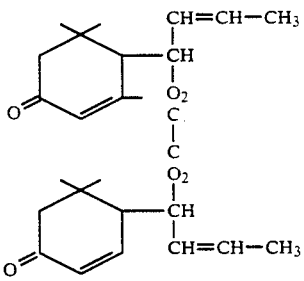

To a chilled (0° C.) solution of 3-oxo-o-damascol (1 g, 4.88 mmol), pyridine (760 mg, 9.6 mmol) and dimethylaminopyridine (120 mg, 0.98 mmol) in 4 mL of ethyl acetate was added dropwise over 30 minutes a solution of oxalyl chloride (366 mg, 2.9 mmol) dissolved in 2 mL of ethyl acetate. Following the procedures of Example VII, the product was recovered and purified by preparative high performance liquid chromatography to yield mg of the title compound. NMR and IR spectra confirmed the structure.

EXAMPLE IX

Ethyl 1-(2,6,6-trimethyl-3-oxo-1-cyclohexenyl)-3-buten-1-yl oxalate

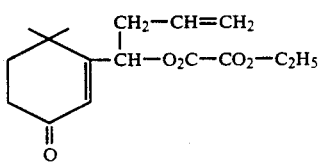

To a chilled (0° C.) solution of 3-(1-hydroxy-3-buten-1-yl)-2,4,4-trimethyl-2-cyclohexanone (250 mg, 1.2 mmol), pyridine (190 mg, 2.4 mmol) and dimethylaminopyridine (29 mg, 0.24 mmol) in 1 mL of ethyl acetate was added dropwise a solution of ethyl oxalyl chloride (198 mg, 1.45 mmol) dissolved in 1 mL of ethyl acetate. Following the procedures of Example VII, the product was recovered and purified by preparative high performance liquid chromatography to yield 260 mg of the title compound. NMR and IR spectra confirmed the structure.

EXAMPLE X

Bis-1-(2,6,6-trimethyl-3-oxo-1-cyclohexenyl)-3-buten-1-yl]oxalate

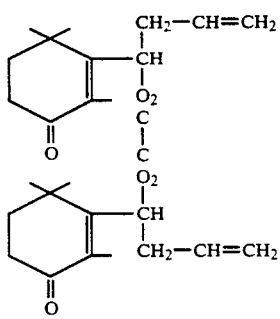

To a chilled (0° C.) solution of 3-(1-hydroxy-3-buten1-yl)-2,4,4-trimethyl-2-cyclohexanone (250 mg, 1.2 mmol), pyridine (190 mg, 2.4 mmol) and dimethylaminopyridine (29 mg, 0.24 mmol) in 1 mL of ethyl acetate was added dropwise over 15 minutes a solution of oxalyl chloride (92 mg, 0.72 mmol) dissolved in 2 mL of ethyl acetate. Following the procedures of Example VII, the product was recovered and purified by preparative high performance liquid chromatography to yield mg of the title compound. The product was recrystallized from 5% ethyl acetate/hexane. NMR and IR spectra confirmed the structure.

EXAMPLE XI

This Example illustrates the preparation of a 4-oxo-β-ionyl carbonate compound of the type disclosed in U.S. Pat. No. 4,827,012.

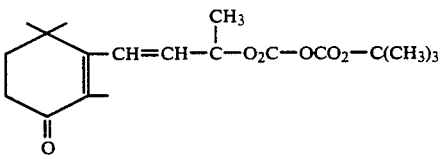

To a chilled solution (0° C.) of 4-oxo-B-ionol (2.04 g, mmol), pyridine (1.6 g, 20 mmol) and dimethylaminopyridine 2 mmol) in 10 mL of ethyl acetate was added dropwise a solution of di-t-butyl dicarbonate (2.6 g, 12 mmol) dissolved in mL of ethyl acetate. The mixture was stirred for about hours at room temperature. Crushed ice was added to the mixture, and the organic phase was separated from the aqueous phase. The organic phase was washed successively with diluted hydrochloric acid, water, saturated sodium bicarbonate solution, and saturated sodium chloride solution. The solution was dried over anhydrous magnesium sulfate. The product was isolated by fractional distillation (b.p. 102° C. 0.35 torr) to provide 1.9 g of the title compound. An analytical sample was purified by preparative high performance liquid chromatography, and NMR and IR spectra confirmed the structure.

EXAMPLE XII

This Example illustrates the superior megastigmatrienone-release efficiency of an invention oxalate ester in comparison with two corresponding monoester compounds.

Methyl 4-oxo-B-ionyl oxalate (invention compound), 4-oxo-β-ionyl acetate and 4-oxo-β-ionyl-3-methylvalerate were pyrolyzed at the injector port of a Varian 3700 gas chromatograph, and the relative amounts of pyrolysates were analyzed by GC on a 15 m DBI7 Megabore column.

Each compound was dissolved in methylene chloride. The injector temperature was set at 250° C., and the sample was introduced into the injector, and the pyrolysates were swept onto the head of the column with no significant holding time in the injector.

The invention methyl 4-oxo-β-ionyl oxalate compound pyrolyzed to a mixture of megastigma-5,7,9-trien-4-one (26%), 4-oxo-β-ionol (1%) and methyl 4-oxo-β-ionyl oxalate (73%). Both 4-oxo-β-ionyl acetate and 4-oxo-β-ionyl 3-methylvalerate showed no decomposition at 250° C.

EXAMPLE XIII

This Example illustrates the superior megastigmatrienone-release efficiency of two invention oxalate esters in comparison with a corresponding carbonate ester.

Methyl 4-oxo-β-ionyl oxalate, bis-(4-oxo-β-ionyl)oxalate and t-butyl 4-oxo-B-ionyl carbonate were pyrolyzed in helium in a quartz tube/furnace pyrolysis unit and the pyrolysates were analyzed by a 30 meter DB-5 fused silica capillary column.

When the furnace temperature was set at 300° C., methyl 4-oxo-β-ionyl oxalate pyrolyzed to give megastigma-5,7,9-trien-4-one (45%) and methyl 4-oxo-β-ionyl oxalate -oxo-β-ionyl carbonate pyrolyzed to give megastigma-5,7,9-trien-4-one (4%) and 4-oxo-β-ionol (96%).

When the furnace temperature was set at 200° C., bis-(4-oxo-β-ionyl) oxalate pyrolyzed to give megastigma-5,7,9-trien-4-one (100%); and t-butyl 4-oxo-B-ionyl pyrolyzed to give megastigma-5,7,9-trien-4-one (6%) and 4-oxo-β-onol (94%).

What is claimed is:

1. A smoking composition comprising an admixture of
   (1) combustible filler selected from natural tobacco, reconstituted tobacco and tobacco substitutes, and
   (2) between about 0.0002-5 weight percent, based on the total weight of filler, of a flavorant-release additive corresponding to the formula:

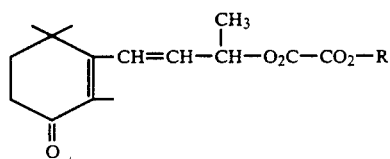

where R is a $C_1-C_8$ alkyl substituent.

2. A smoking composition in accordance with claim 1 wherein the flavorant-release additive is methyl 4-oxo-β-ionyl oxalate or ethyl 4-oxo-β-ionyl oxalate.

3. A smoking composition comprising an admixture of
   (1) combustible filler selected from natural tobacco, reconstituted tobacco and tobacco substitutes, and
   (2) between about 0.0002-5 weight percent, based on the total weight of filler, of bis-(4-oxo-β-ionyl) oxalate as a flavorant-release additive:

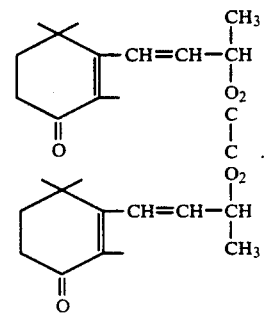

4. A smoking composition comprising an admixture of
   (1) combustible filler selected from natural tobacco, reconstituted tobacco and tobacco substitutes, and
   (2) between about 0.0002-5 weight percent, based on the total weight of filler, of a flavorant-release additive corresponding to the formula:

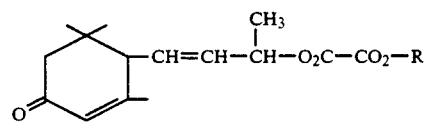

where R is a $C_1-C_8$ alkyl substituent.

5. A smoking composition in accordance with claim 4 wherein the flavorant-release additive is methyl 3-oxo-α-ionyl oxalate or ethyl 3-oxo-α-oxalate.

6. A smoking composition comprising an admixture of
   (1) combustible filler selected from natural tobacco, reconstituted tobacco and tobacco substitutes, and
   (2) between about 0.0002-5 weight percent, based on the total weight of filler, of bis-(3-oxo-α-ionyl) oxalate as a flavorant-release additive:

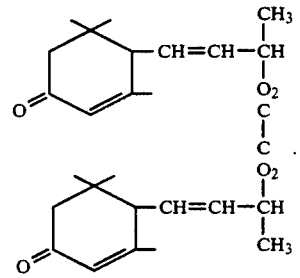

7. A smoking composition comprising an admixture of
   (1) combustible filler selected from natural tobacco, reconstituted tobacco and tobacco substitutes, and (2) between about 0.0002-5 weight percent, based on the total ,/ weight of filler, of a flavorant-release additive corresponding to the formula:

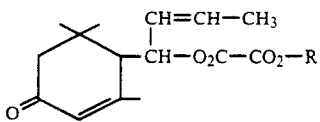

where R is a $C_1-C_8$ alkyl substituent.

8. A smoking composition in accordance with claim 7 wherein the flavorant-release additive is methyl 3-oxo-α-damascyl 9. A smoking composition comprising an admixture of
   (1) combustible filler selected from natural tobacco, reconstituted tobacco and tobacco substitutes, and
   (2) between about 0.0002-5 weight percent, based on the total weight of filler, of bis-(3-oxo-α-damascyl) oxalate as a flavorant-release additive:

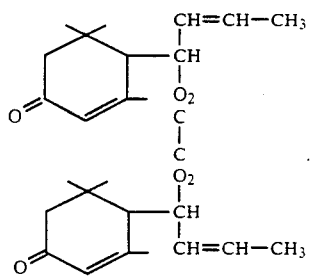

10. A smoking composition comprising an admixture of
    (1) combustible filler selected from natural tobacco, reconstituted tobacco and tobacco substitutes, and
    (2) between about 0.0002-5 weight percent, based on the total weight of filler, of a flavorant-release additive corresponding to the formula:

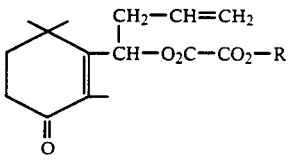

where R is a $C_1-C_8$ alkyl substituent.

11. A smoking composition in accordance with claim 10 wherein the flavorant-release additive is ethyl 1-(2,6,6-trimethyl-3-oxo-1-cyclohexenyl)-3-buten-1-yl oxalate.

12. A smoking composition comprising an admixture of
    (1) combustible filler selected from natural tobacco, reconstituted tobacco and tobacco substitutes, and
    (2) between about 0.0002-5 weight percent, based on the total weight of filler, of bis-[1-(2,6,6-trimethyl-3-oxo-1-cyclohexenyl)-3-buten-1-yl]oxalate as a flavorant additive:

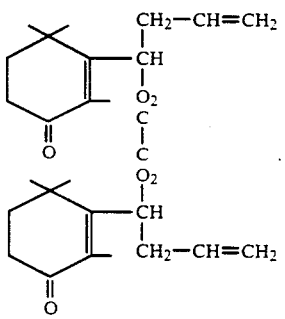

* * * * *